United States Patent [19]
Willey et al.

[11] Patent Number: 6,156,529
[45] Date of Patent: Dec. 5, 2000

[54] METHOD FOR SPECIFICALLY MARKING A PROTEIN

[75] Inventors: Kevan Willey, Hamburg; Heike Obermann-Pless, Lüneburg; Nicholas Hunt, Neu-Wulmstorf; Karsten Henco, Erkrath, all of Germany

[73] Assignees: EVOTEC BioSystems AG; IHF Institut für Hormon-und Fortpfianzungsforschung GmbH, both of Hamburg, Germany

[21] Appl. No.: 09/367,861

[22] PCT Filed: Mar. 5, 1998

[86] PCT No.: PCT/EP98/01229

§ 371 Date: Sep. 2, 1999

§ 102(e) Date: Sep. 2, 1999

[87] PCT Pub. No.: WO98/39660

PCT Pub. Date: Sep. 11, 1998

[30] Foreign Application Priority Data

Mar. 6, 1997 [DE] Germany .............. 197 09 168
Oct. 29, 1997 [DE] Germany .............. 197 47 632

[51] Int. Cl.[7] .............. C12Q 1/26; C12Q 1/00; G01N 33/53

[52] U.S. Cl. .............. 435/25; 435/4; 435/7.5; 435/968

[58] Field of Search .............. 435/25, 4, 7.5, 435/968

[56] References Cited

FOREIGN PATENT DOCUMENTS

98/01229  3/1998  European Pat. Off. .
19709168  3/1997  Germany .
19747632  3/1998  Germany .

*Primary Examiner*—Louise N. Leary
*Attorney, Agent, or Firm*—Jacobson, Price, Holman & Stern, PLLC

[57] ABSTRACT

The present invention relates to a method for the specific labeling of a protein containing selenocyst(e)ine and/or cyst(e)ine groups, comprising the following steps:

at least one incubation of a protein-containing sample with at least one modifying agent specific for selenocyst(e)ine and/or cyst(e)ine groups, followed by at least one further incubation of said protein-containing sample with at least one labeling agent specific for selenocyst(e)ine and/or cyst(e)ine groups;

wherein at least one substance interacting with said protein is added prior to and/or during and/or after at least one of said incubations.

14 Claims, 15 Drawing Sheets

METHOD FOR SPECIFICALLY MARKING A PROTEIN

The present invention relates to a method for the specific labeling of a protein containing selenocyst(e)ine and/or cyst(e)ine groups.

The examination of receptors, such as the G protein coupled receptors, the polypeptide chain of which folds into a structure with seven membrane-spanning helices is of great importance in terms of both science and economy. These so-called 7-transmembrane receptors are a large group of receptors which are very old phylogenetically and the amino acid sequence of which contains characteristic cysteines. The corresponding ligands belong to a wide variety of chemical classes of substances and molecular sizes, from lipids, metal ions and monoamines to peptides and proteins. However, to date, little is known about possible structural changes of such receptors which represent the link between ligand binding and signal transduction.

It is believed that ligand-induced conformational changes of the 7-transmembrane receptors are involved in the initial step of the dissociation of the heterotrimeric G protein complex with exchange of GDP/GTP. Schwartz and Rosenkilde (TiPS, Vol. 17, 1996) present a model in which the capability of stabilizing an active receptor conformation is mentioned as the only requirement for a new agonist, resulting in the conclusion that a common "lock" for all the "keys" in the superfamily of 7-transmembrane receptors does not exist.

Generally, in the examination of proteins, but also, in particular, in the investigation of the signal cascade, cysteine-specific reagents are used in order to shed light upon the functional and structural properties of the cysteines (Creighton, "Proteins", Freeman & Co., 1984). Korner et al. (The Journal of Biological Chemistry, Vol. 257, No. 7, pp. 3389–3396, 1982) describe a method for examining the $\beta_2$-adrenergic receptor using N-ethylmaleinimide (NEM). In order to react thiol groups which are already exposed prior to the actual experiment, the membrane samples were pre-treated with NEM in the presence of the antagonist propranolol in a first process step. In a further process step, they were incubated with [$^3$H]isoproterenol with addition of NEM. In particular, the authors come to the conclusion that NEM interacts, not with the receptor itself, but with an associated component, the G protein. According to Korner et al., specific thiol groups of the G protein are being exposed when the G protein interacts with the hormone-activated receptor. Accordingly, the method of Korner et al. is not suitable for labeling the actual receptor.

André et al. (Biochemical Pharmacology, Vol. 31, No. 22, 3657–3662, 1982) describe the effect of NEM on agonist-induced conformational changes of the $\beta$-adrenergic receptor. The process performed on membrane preparations is characterized by three incubation steps: incubation with NEM, followed by incubation with NEM in the presence of the agonist (−)-isoproterenol, followed by incubation with the labeled antagonist (−)-[$^3$H]DHA. André et al. observed that the effects brought about by NEM can also be induced by GTP in their experiments, so that evidently G proteins are critically involved.

Lipson et al. (Biochemistry 1986, 25, 5678–5685) describe a method for examining the glucagon receptor N protein complex using N-ethylmaleinimide and other reagents which alkylate thiols. It could be demonstrated, for example, that the presence of NEM prior to, during or after the association reaction of $^{125}$I-glucagon with partially purified, protein-containing liver membranes promotes the release of bound hormone in a subsequent dissociation reaction.

In a survey article, in which the use of the alkylating agent N-ethylmaleinimide (NEM) in the investigation of G protein coupled receptors was last mentioned (Lefkowitz et al., Ann. Rev. Biochem. 52, 159–86, 1983), the authors note that it is uncertain whether the critical sulfhydryl groups are localized on the receptor, on the G protein, or even on both components.

Today, the particular importance of the cysteines in the $\alpha\beta$-heterotrimer of the G protein is generally known. Corresponding examinations have been performed, e.g., by Garcia-Higuera (J. Biol. Chem., Vol. 257, No. 1, 528–535, 1996) using crosslinking agents and by SDM (site-directed mutagenesis).

Li et al. (The Journal of Biological Chemistry, Vol. 267, No. 11, 7570–7575, 1992) examined the importance of thiol groups to the binding of the neuropeptide Y to the $Y_2$ receptor.

Examinations regarding the importance of disulfide bridges and thiol groups to the binding of the thyrotropin-releasing hormone (TRH) to the TRH receptor have been performed by Cook et al. (Endocrinology, Vol. 137, No. 7, 2851–2858, 1996). Dithiothreitol (DTT), a disulfide-bridge reducing agent, and p-CMB, a thiol-group blocking substance, reduce the specific TRH binding in a dose-dependent way.

Approaches to the examination of conformational changes of G protein coupled receptors are often indirect in nature, i.e., for example, the effect of the receptor conformation on the GTPase activity of the G protein or the activity of effector enzymes is examined.

Gether et al. (The Journal of Biological Chemistry, Vol. 270, No. 47, issue of November 24, pp. 28268–28275, 1995), however, describe a method for the fluorescent labeling of the purified $\beta_2$-adrenergic receptor with the purpose of enabling ligand-induced conformational changes of this G protein coupled receptor to be directly recognized. Thus, the receptor expressed in SF-9 insect cells was first subjected to purification, prior to being labeled with the cysteine-specific fluorescent marker N,N'-dimethyl-N-(iodoacetyl)-N'-(7-nitrobenz-2-oxa-1,3-diazol-4-yl)ethylenediamine (IANBD). The fluorescence of IANBD is highly dependent on the polarity of the dye environment and can therefore be employed as an indicator of conformational changes of the receptor. Thus, a slight decrease in fluorescent emission could be observed upon the binding of the agonist isoproterenol to the $\beta_2$-adrenergic receptor. A drawback of the method described by Gether et al. is, in particular, the extremely laborious and time-consuming multistep purification of the receptor.

A great number of survey articles on the superfamily of nuclear receptors have appeared just recently (Cell, Vol. 83, 835–839, 841–850, 851–857, 1995), so that the function of these receptors shall not be further dealt with in the present application.

It has been the object of the present invention to provide a method for the specific labeling of protein-containing samples, such as receptors, especially transmembrane receptors, but also soluble receptors.

The object of the invention is achieved by a method according to claim 1. Advantageous embodiments of the invention are described in the subclaims.

The method according to the invention is characterized by the following process steps:
  at least one incubation of a protein-containing sample with at least one modifying agent specific for selenocyst(e)ine and/or cyst(e)ine groups, followed by
  at least one further incubation of said protein-containing sample with at least one labeling agent specific for selenocyst(e)ine and/or cyst(e)ine groups;

wherein at least one substance interacting with said protein is added prior to and/or during and/or after at least one of said incubations.

The groups mentioned may be present in the protein essentially either in reduced form (selenocysteines or cysteines) or in oxidized form (selenocystines or cystines). The spellings "selenocyst(e)ine" and "cyst(e)ine" mean that the groups mentioned can be present essentially in one of the redox states mentioned.

The method according to the invention makes use of the fact that apparently inaccessible selenocyst(e)ines and/or cyst(e)ines of the protein can be labeled through the activation or conformational change of the protein induced by the addition of a substance during incubation with a labeling agent specific for selenocyst(e)ine and/or cyst(e)ine groups, or the degree of labeling of the protein and/or properties of the labeling agent are changed thereby.

For the detection of a thus induced activation or conformational change, it is desirable to modify the selenocyst(e)ines and/or cyst(e)ines already accesible, in particular, prior to the addition of said substance interacting with the protein in order to reduce the background and to increase the detection efficiency. This is achieved by the one or more additions of a modifying agent specific for selenocyst(e)ine and/or cyst(e)ine groups according to the invention. Thus, when the method according to the invention is applied to 7-transmembrane receptors, negative allosteric effects of the G protein on the receptor which accelerate the agonist dissociation can be advantageously suppressed, or interfering cysteine proteases which can cause degradation of the agonist receptor complex can be inactivated. Said modifying and labeling agents specific for selenocyst(e)ine and/or cyst(e)ine groups may be added in stoichiometric amounts. According to another preferred embodiment of the method according to the invention, they are added in excess. Excess modifying agent can be advantageously removed prior to the incubation of the protein-containing sample with a labeling agent, especially by centrifugation or by washing steps, or it may be inactivated by the addition of chemicals containing cysteine, selenocysteine or SH groups.

As an advantage over the prior art, the method according to the invention is characterized by being particularly suitable for use in high-throughput screening due to the use of a unique labeling agent and enabling the detection of new ligands for protein-containing samples, especially known ones, or vice versa. An accelerated functional validation of orphan receptors, especially 7-transmembrane orphan receptors, as target/lead systems and of known receptors in pharma screening for new agonists or antagonists by a general test procedure is of utmost economic importance. Thus, for example, agonists for an orphan receptor with unknown function can be identified from a ligand library using the method according to the invention. The method according to the invention allows to differentiate between agonists and antagonists. Thus, a detection of antagonists can be achieved due to the inhibition of the agonist-induced labeling or by the detection of a substrate/inhibitor interaction.

The method according to the invention can be used in a screening procedure for determining substances interacting with a protein to be examined. Such substances may be derived, for example, from extracts of natural substances. Currently, commercial vegetable drugs mostly contain raw extracts, chromatographic fractions, mixtures or emulsions of substances. It is generally considered that at least one quarter of the drugs employed today in industrial countries are of vegetable origin or are prepared after a model of substances contained in plants. However, the substances may also be derived from the reservoir of substances provided by combinatory chemistry. Using this method, several millions of structurally related substances can be produced in a very short time. These are often preselected compounds for which it is to be expected, from the properties of the starting materials, that at least some of them exhibit the desired activity in a more or less pronounced form. The most effective compounds can be selected by screening the resulting pool of compounds using the method according to the invention.

Using the method according to the invention, it is also possible to test proteins, especially those which have not been further characterized, for a potential interaction with substances, especially known ones, in a screening procedure.

Medicinal substances preferably act on enzymes, receptors, transporters, ion channels and signal proteins. Some inhibit the reactions catalyzed by enzymes, while others bind to receptors and thereby either, as agonists, cause the same effect as the endogenous messengers, or, as antagonists, have the very opposite effect by preventing normal ligands from accessing the site or impeding the formation of a given three-dimensional structure of the receptor. Similarly, with transporters, the substances actually to be transported are displaced. In the case of ion channels, the drug stabilizes either the open or the closed form. Finally, signal proteins control the activitty of enzymes, receptors or ion channels and can also be influenced by medicinal substances. In all these cases, it is critical that the medicinal substance communicate with the biological structures or block the interaction with the actually intended agent.

The method according to the invention offers the possibility to test substances as well as proteins for whether they interact with each other.

It may be desirable to adjust the incubation times to the kinds of modifying and labeling agents specific for selenocyst(e)ine and/or cyst(e)ine groups. Further, it is possible, after incubation of the protein-containing sample with the modifying agents specific for selenocyst(e)ine and/or cyst(e)ine groups, to add only the substance first for preequilibration and to add the labeling agent specific for selenocyst(e)ine and/or cyst(e)ine groups only at a later time. The addition of the labeling agent may be done once or several times. However, it may also be desirable first to add the substance interacting with the protein to the sample and to add the modifying agent and the labeling agent in subsequent steps. Similarly, the other times of addition of the substance interacting with the protein as mentioned in claim 1 may also be advantageous.

According to another embodiment of the method according to the invention, transmembrane receptors, in particular, such as G protein coupled 7-transmembrane receptors, are specifically labeled, or a ligand-induced activation and/or deactivation and/or conformational change of these receptors is detected.

Reagents specific for cyst(e)ine groups or selenocyst(e)ine groups are known from the literature (Creighton, "Proteins", Freeman & Co., 1984) and can accordingly be employed in the method according to the invention. In this connection, experiments have been performed with various reagents specific for selenocyst(e)ines or cyst(e)ines (including iodoacetate, iodoacetamide, diamide, monovalent and divalent maleinimides, such as NEM, various metal compounds, DTT, $NaBH_4$, pyridoxal phosphate). Preferably, alkylating reagents, such as N-ethylmaleinimide (NEM), may be used in the method according to the invention. It may further be preferred to perform an incubation of the protein-containing sample with a reducing agent, such as β-mercaptoethanol or dithiothreitol, in order to influence cysteines which are linked to one another through disulfide bridges.

Through the combination of alkylating and reducing cyst(e)ine-reactive reagents, it is possible to further optimize the reaction conditions. Reagents of different hydrophobicities and sizes have different membrane permeabilities, which may be considered in the method according to the invention.

The substitution of cysteines by selenocysteines in proteins is described in the more recent literature (Müller et al., Biochemistry, 33, 3404–3412, 1994; Ursini et al., Methods in Enzymology, Vol. 252, 38–53, Academic Press, 1995; Bj örnstedt et al., Methods in Enzymology, Vol. 252, 209–219, Academic Press, 1995).

A "labeling agent specific for selenocyst(e)ine or cyst(e)ine groups" within the meaning of the invention includes any reagents which will react with selenocyst(e)ine or cyst(e)ine and which contain a detectable portion. The detectable portion may be selected depending on the detection system, e.g., haptens for immunological detection, multivalent, preferably divalent, functional groups for a cross-linking reaction. Further, radio-labeled substances may also be used, or detection may be effected using biotin/streptavidin or avidin. It may be preferred to use biotin, as in Example 1, so that the specific labeling of a receptor can be detected by a Western blot using appropriate antibodies. The labeling agent specific for selenocyst(e)ine or cyst(e)ine may preferably be luminescent. Then, for the detection of the labeling having been effected and/or an activation and/or deactivation and/or conformational change of the receptor, the method of fluorescence correlation spectroscopy (WO 94/16313) and other confocal fluorescence techniques, as described in the publication WO 96/13744 and in the European Patent Application 96 116 373.0, can be employed. The latter application suggests a method for analyzing samples by repeatedly measuring the number of photons per defined time interval in light which is emitted, scattered and/or reflected by the particles in the sample and determining the distribution of the number of photons in the respective time intervals, characterized in that the distribution of the molecular brightness of the particles is determined from the distribution of the numbers of photons. There may also be used a method for analyzing samples which relies on the repeated measurement of the length of time intervals between photons, determining the distribution of properties of the particles, such as the distribution of the molecular brightness, from the distribution of the lengths of the time intervals. It may also be desirable to employ a detection method which determines at least two properties of the labeled particles from at least two-dimensional intermediary statistical data. Such a method is explained in more detail in the European Patent Application 97 109 353.9. It may further be preferred to employ a signal analyzing method for the detection of the labeling reaction, which method is described in the German Patent Application 196 49 048.0 and in the International Patent Application PCT/EP 97/06622. Said method is a method for differentiating or detecting particles in a sample in which several classes of particles may be present by identifying signal segments of time-resolved, optical raw signals from the sample on the basis of single photon detection (single pulse detection), wherein the sample contains at least two classes of particles;

the sample is illuminated by a light source;

the optical raw signals emitted by the sample, which are derived from at least one measuring volume element V, $V \leq 10^{-12}$ l, are detected with at least one detector unit;

at least one particle generates a signal fraction during its residence in the measuring volume element;

a signal segment of the optical raw signals is determined by the particle's actively and/or passively entering and then leaving again the measuring volume element;

the optical raw signals are segmented into arbitrary segments;

at least one set of statistical data based on the optical raw signals is established for at least one arbitrarily chosen segment; and said at least one set of statistical data or at least one combination of several sets of statistical data is evaluated for the presence of features characteristic of the signal fraction from at least one class of particles.

Further, it may be preferred to detect the labeling reaction using the method for determining predefined properties of target particles of a sample medium as described in the German Patent Application 197 02 914.0. The disclosures of the above mentioned patent applications, especially with respect to the detection and signal analyzing methods and devices suitable therefor as explained therein, are incorporated herein by reference.

The provision of the protein-containing sample can be done, in particular, using (recombinant) cells, tissues, vesicles or artificial membranes. Advantageously, the method according to the invention does not forcibly require purification of the components involved.

BRIEF DESCRIPTION OF THE DRAWINGS

FIG. 1 illustrates the effect of NEM on the interaction of TSH with the TSH receptor. $^{125}$I-labeled bovine TSH (B) or HeLa cells transfected with human TSH receptor (C) were incubated at room temperature with 3 mM NEM for 20 min. After dilution or washing steps, untreated receptor or radio-ligand was added. The assay was incubated at 30° C. over night, and the receptor fraction was subsequently precipitated for determining the bound $^{125}$I-TSH. (D) shows the result of an assay performed in the presence of 3 mM NEM, neither the hormone nor the receptor fraction having previously been pretreated with NEM. (A) shows the control incubation without any NEM incubation.

FIG. 2 illustrates the effect of DTT on the interaction of TSH with the TSH receptor. $^{125}$I-labeled bovine TSH (B) or HeLa cells transfected with human TSH receptor (C) were incubated at room temperature with 1 mM DTT for 20 min. After dilution or washing steps, untreated receptor or radio-ligand was added. The assay was incubated at 30° C. over night, and the receptor fraction was subsequently precipitated for determining the bound $^{125}$I-TSH. (D) shows the result of an assay performed in the presence of 1 mM DTT, neither the hormone nor the receptor fraction having previously been pretreated with DTT. (A) shows the control incubation without any DTT incubation.

FIG. 3 represents TSH binding curves with untreated receptor as a control (a), with a receptor pretreated with 3 mM NEM (b), with a receptor treated with 3 mM NEM only in the subsequent binding assay (c), and with a receptor which has been both pretreated with 3 mM NEM and treated with 3 mM NEM in the assay (d).

FIG. 4 shows the results of the Western Blots with respect to the detection of the TSH FLAG receptor as a control (anti-FLAG blot) as well as the detection of the cysteine-specific labeling agent NEM-biotin bound to the TSH receptor. HeLa cells transfected with the TSH FLAG receptor were incubated once with each of different NEM concentrations for 30 minutes (column 1: HeLa cells without TSH FLAG receptor, no NEM pretreatment; column 2: HeLa cells with TSH FLAG receptor, no NEM pretreatment; column 3: HeLa cells with TSH FLAG receptor, pretreatment with 100 μM NEM; column 4: HeLa cells with TSH FLAG receptor, pretreatment with 1 mM NEM; column 5: HeLa cells with TSH FLAG receptor, pretreatment with 10 mM NEM). After removing the NEM solutions and washing the cells, the cells were incubated with 100 nM TSH and 1 mM NEM-biotin for one hour. After treatment with cell lysis buffer, the TSH FLAG receptor was immunoprecipitated by means of anti-FLAG antibodies. The immunoprecipitate was divided into two fractions which were both further treated by SDS PAGE. The separated proteins were transferred to nitrocellulose membranes for the Western blots (anti-FLAG and anti-biotin). Detection was effected by using a second enzyme-coupled antibody (anti-Ig). The TSH FLAG receptor shows a characteristic pattern of bands (anti-FLAG blot) consisting of a major band and two minor bands, which pattern remained unaffected by the NEM treatment. The labeling of the TSH receptor with NEM-biotin increases with increasing concentrations of NEM in the pretreatment (anti-biotin blot). Higher NEM concentrations can influence accordingly more cysteine SH groups already present, so that less NEM-biotin is lost due to non-specific binding reactions on the cells. Consequently, relatively more NEM-biotin is available for the labeling of the SH groups made accessible by a ligand-induced activation and/or conformational change of the receptor.

FIG. 5 shows the results of the Western Blots after different NEM and TSH treatments of the TSH receptor. The cells were divided into three fractions and pelletized with buffer (columns 1 to 3) or with 3 mM NEM (columns 4 to 6: incubation for 20 minutes; columns 7 to 9: incubation for 20 hours) prior to incubation. Then, each sample was further treated as follows: incubation for one hour with buffer (columns 1, 4 and 7), incubation for one hour with 100 nM TSH (columns 2, 5 and 8), or incubation for 22 hours with 100 nM TSH (columns 3, 6 and 9). This was respectively followed by incubation for one hour with 1 mM NEM-biotin. The samples were centrifuged, washed several times, lysed and, after SDS PAGE, examined by a Western blot. The TSH receptor was immunoprecipitated with anti-FLAG antibodies and examined for biotin binding in the blot. Columns 1 and 2 show a weak NEM-biotin labeling of the receptor which can be increased by incubation with TSH for one hour (column 2). Columns 4 to 6 show, on the one hand, the increased labeling of the receptor brought about by incubation with NEM for 20 minutes and, on the other hand, furnish evidence of the higher labeling rate of the receptor achieved by TSH incubation. The specificity of the TSH-induced NEM-biotin labeling of the receptor is evidently lost during long NEM incubation times (columns 7 to 9).

FIG. 6 illustrates the effect of NEM on the interaction of a ligand with the β$_2$-adrenergic receptor. The agonist (-)-isoproterenol (B) and A431 cells expressing the human β$_2$-adrenergic receptor (C) were incubated at room temperature with 3 mM NEM for 20 min. After dilution or washing steps, untreated receptor or ligand was added in the presence of $^{125}$I-ICYP. The assay was incubated at 30° C. for 40 min, and the receptor fraction was subsequently precipitated for determining the bound $^{125}$I-ICYP. The pretreatment of the agonist or the receptor with NEM has only a small effect on the binding. (D) shows the result of an assay performed in the presence of 3 nM NEM, neither the hormone nor the receptor fraction having previously been pretreated with NEM. (A) shows the control incubation without any NEM incubation.

FIG. 7 illustrates the but small effect of DTT on the interaction of a ligand with the β$_2$-adrenergic receptor. The agonist (-)-isoproterenol ((B) and A431 cells expressing the human β$_2$-adrenergic receptor (C) were incubated at room temperature with 8 mM DTT for 20 min. After dilution or washing steps, untreated receptor or ligand was added in the presence of $^{125}$I-ICYP. The assay was incubated at 30° C. for 40 min, and the receptor fraction was subsequently precipitated for determining the bound $^{125}$I-ICYP. The pretreatment of the agonist or the receptor with NEM has only a small effect on the binding. (D) shows the result of an assay performed in the presence of 8 mM DTT, neither the hormone nor the receptor fraction having previously been pretreated with DTT. (A) shows the control incubation without any DTT incubation.

Figure 1:
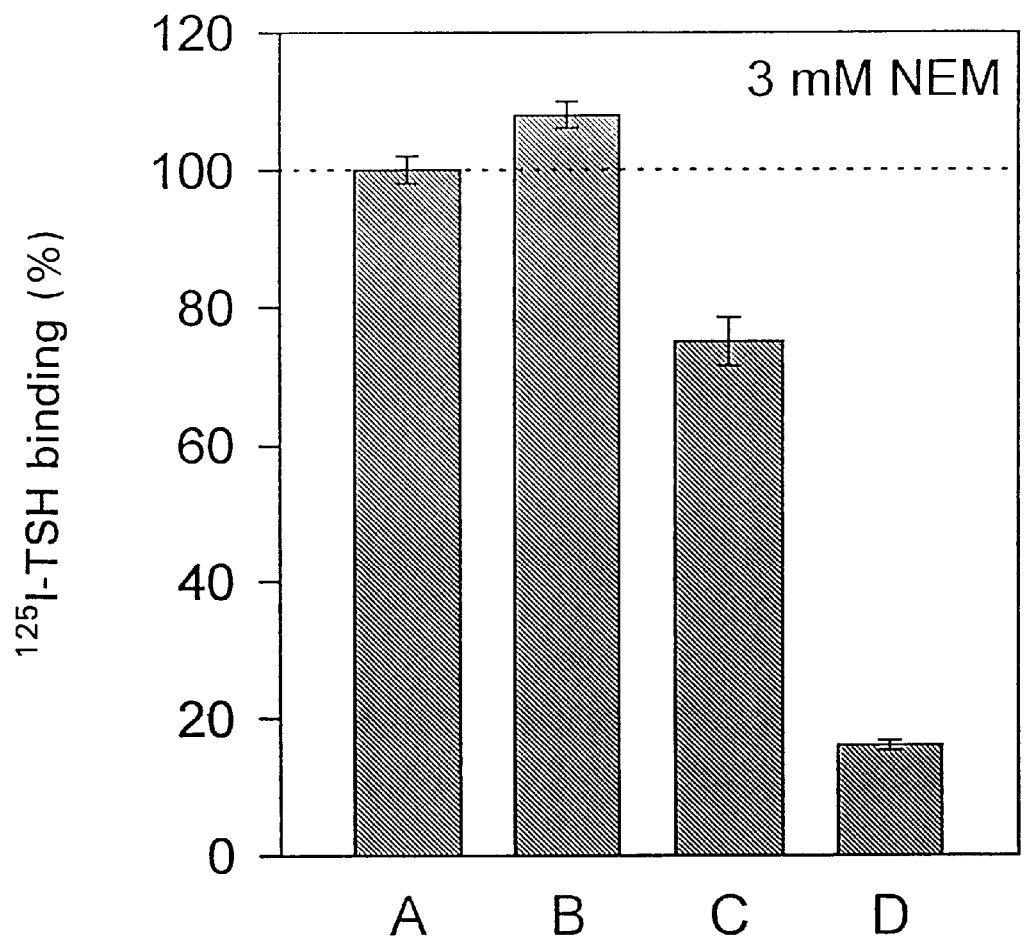
FIG. 1 shows the effect of NEM on the interaction of thyrotropin (TSH) with the TSH receptor.
Figure 2:
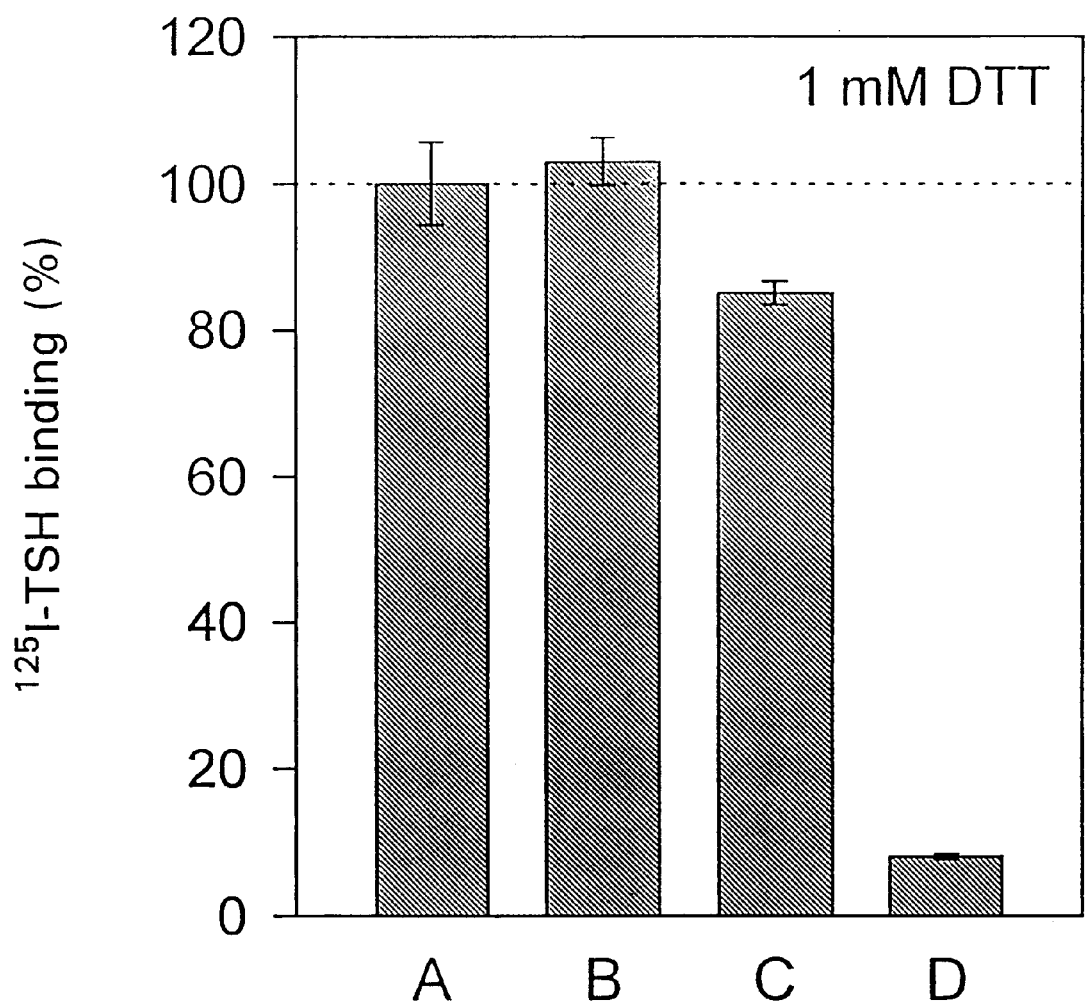
FIG. 2 shows the effect of DTT on the interaction of thyrotropin (TSH) with the TSH receptor.
Figure 3:
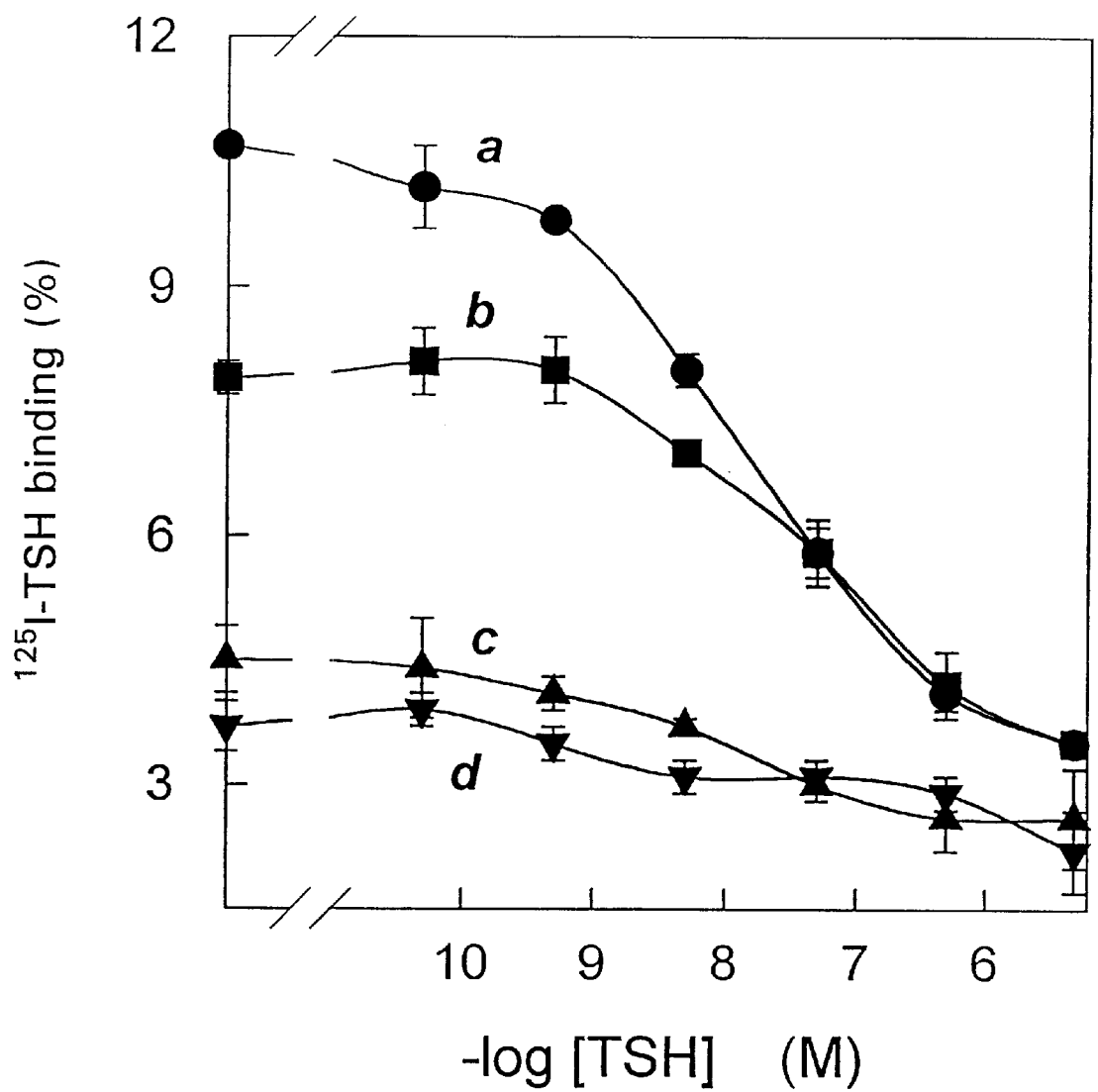
FIG. 3 shows TSH binding curves.
Figure 4:
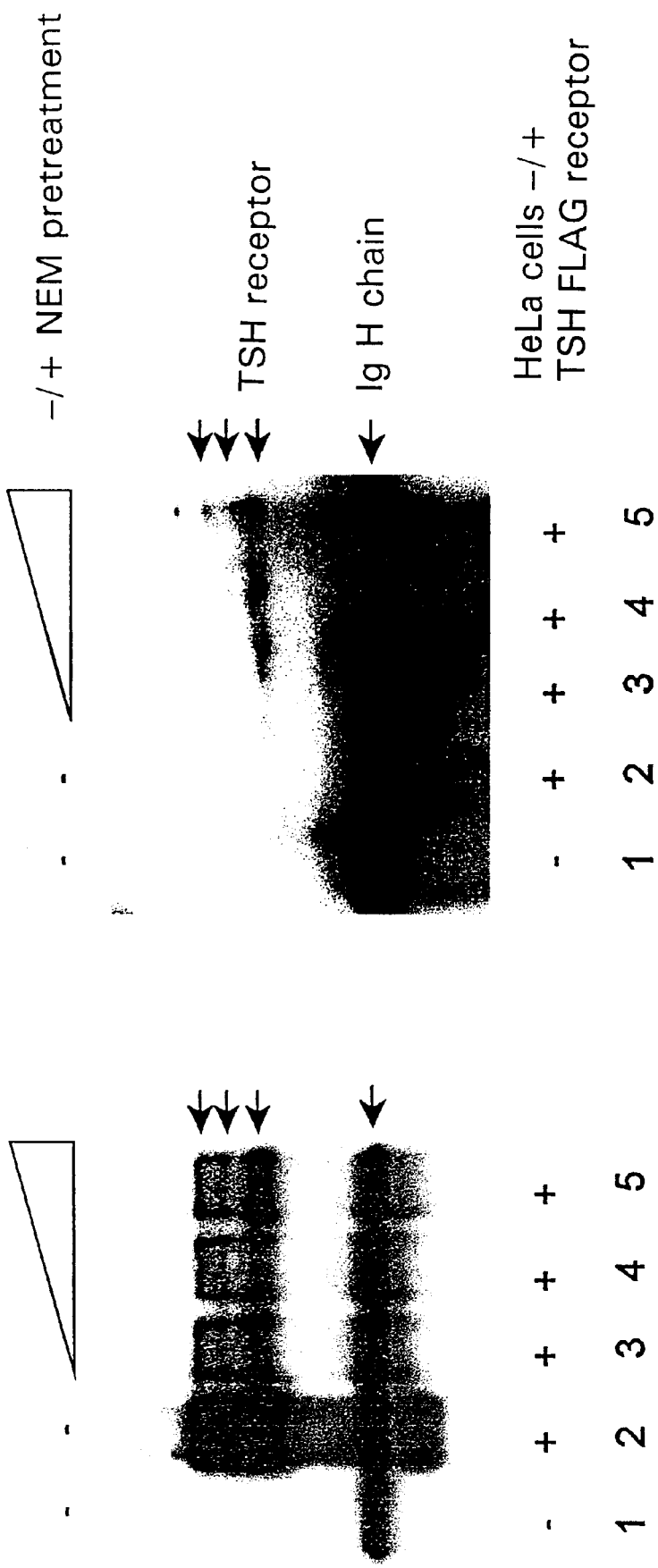
FIG. 4 shows the results of Western Blots with respect to the detection of the TSH FLAG receptor and the binding of biotin to the receptor.
Figure 5:
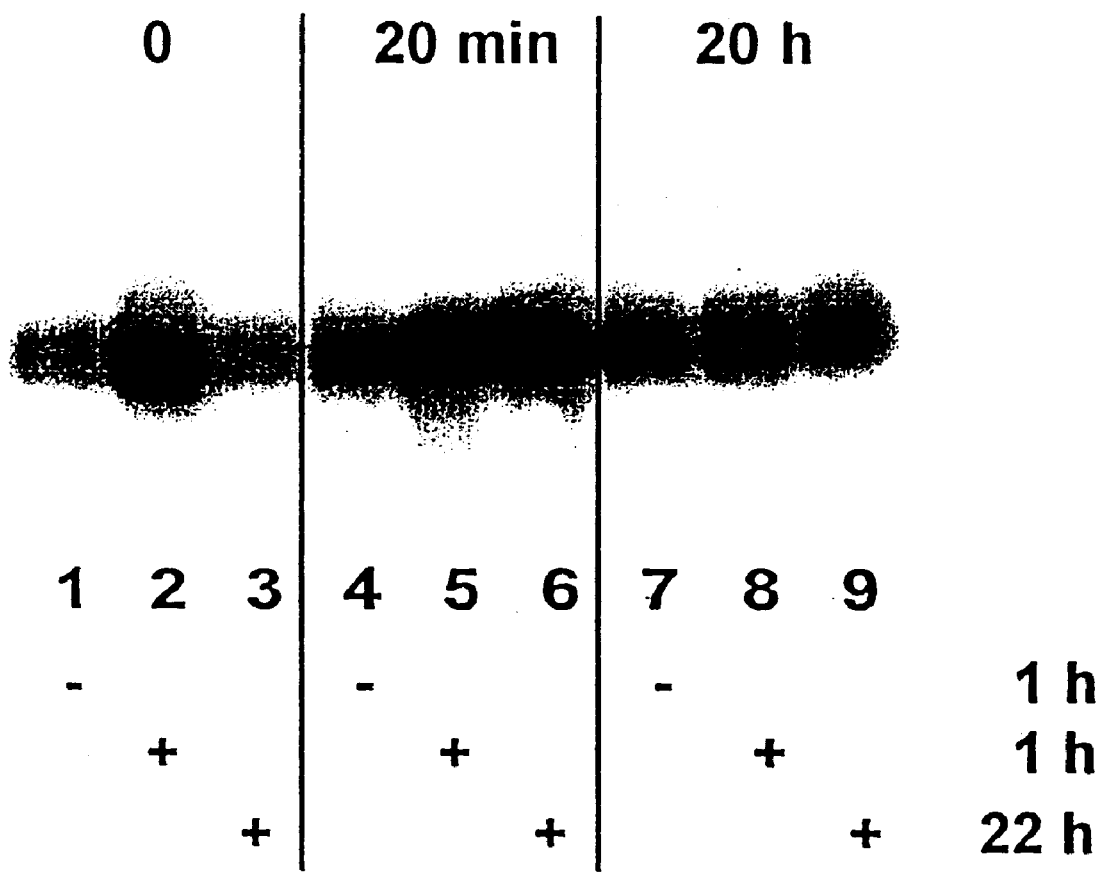
FIG. 5 shows the results of the Western Blots after different NEM and TSH treatments of the TSH receptor.
Figure 6:
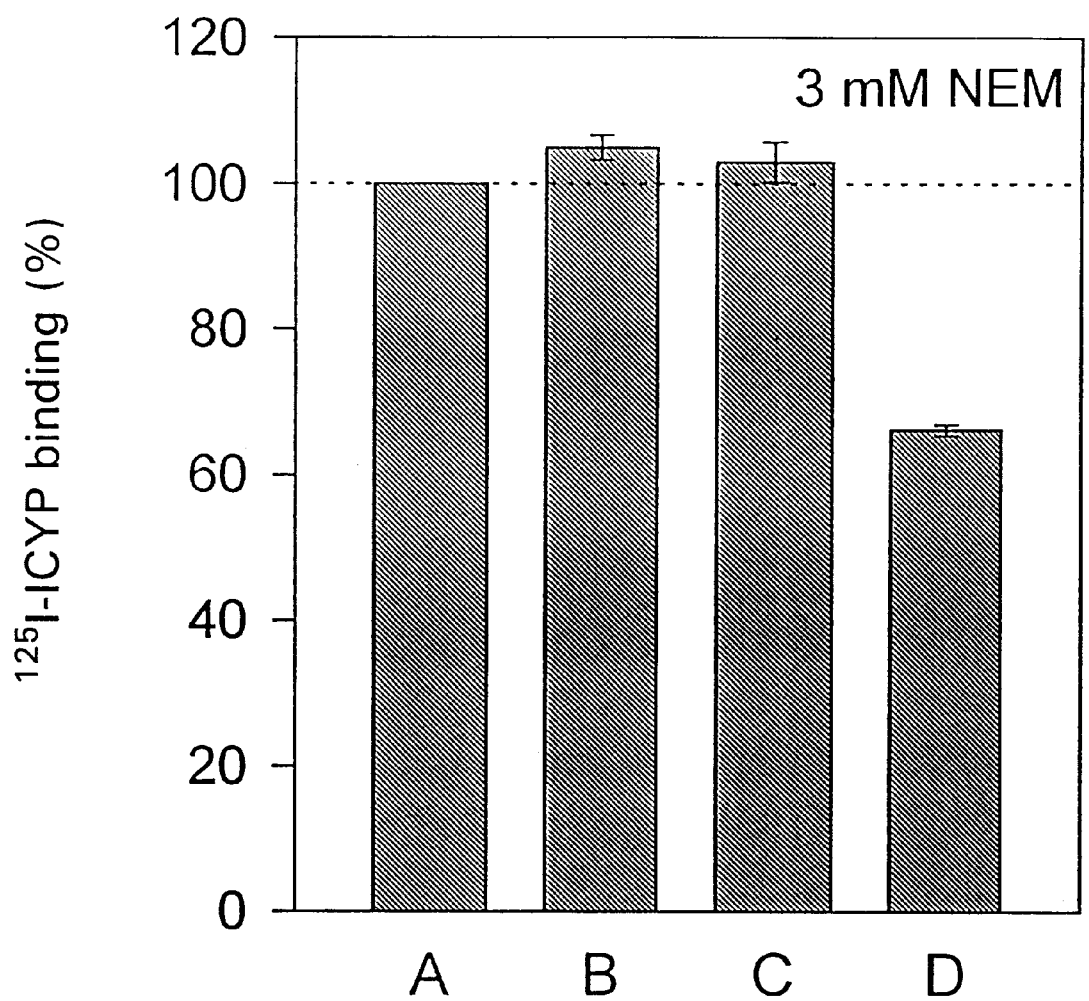
FIG. 6 shows the effect of NEM on the interaction of $^{125}$I-labeled antagonist (iodocyanopindolol, ICYP) with the $\beta_2$-adrenergic receptor in the presence of the agonist (−)-isoproterenol (100 nM).
Figure 7:
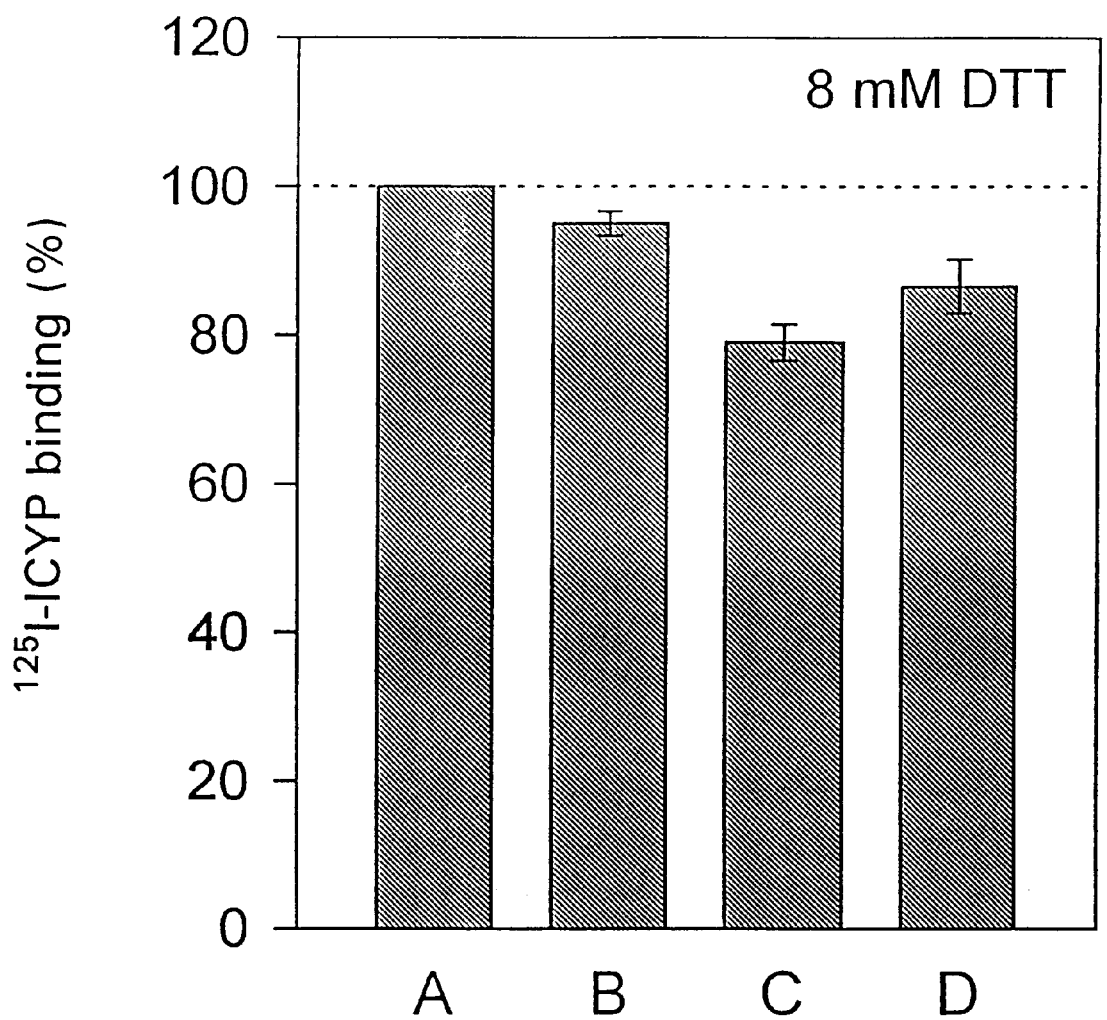
FIG. 7 shows the effect of DTT on the interaction of a $^{125}$I-labeled antagonist (iodocyanopindolol, ICYP) with the $\beta_2$-adrenergic receptor in the presence of the agonist (−)-isoproterenol (100 nM).
Figure 8:
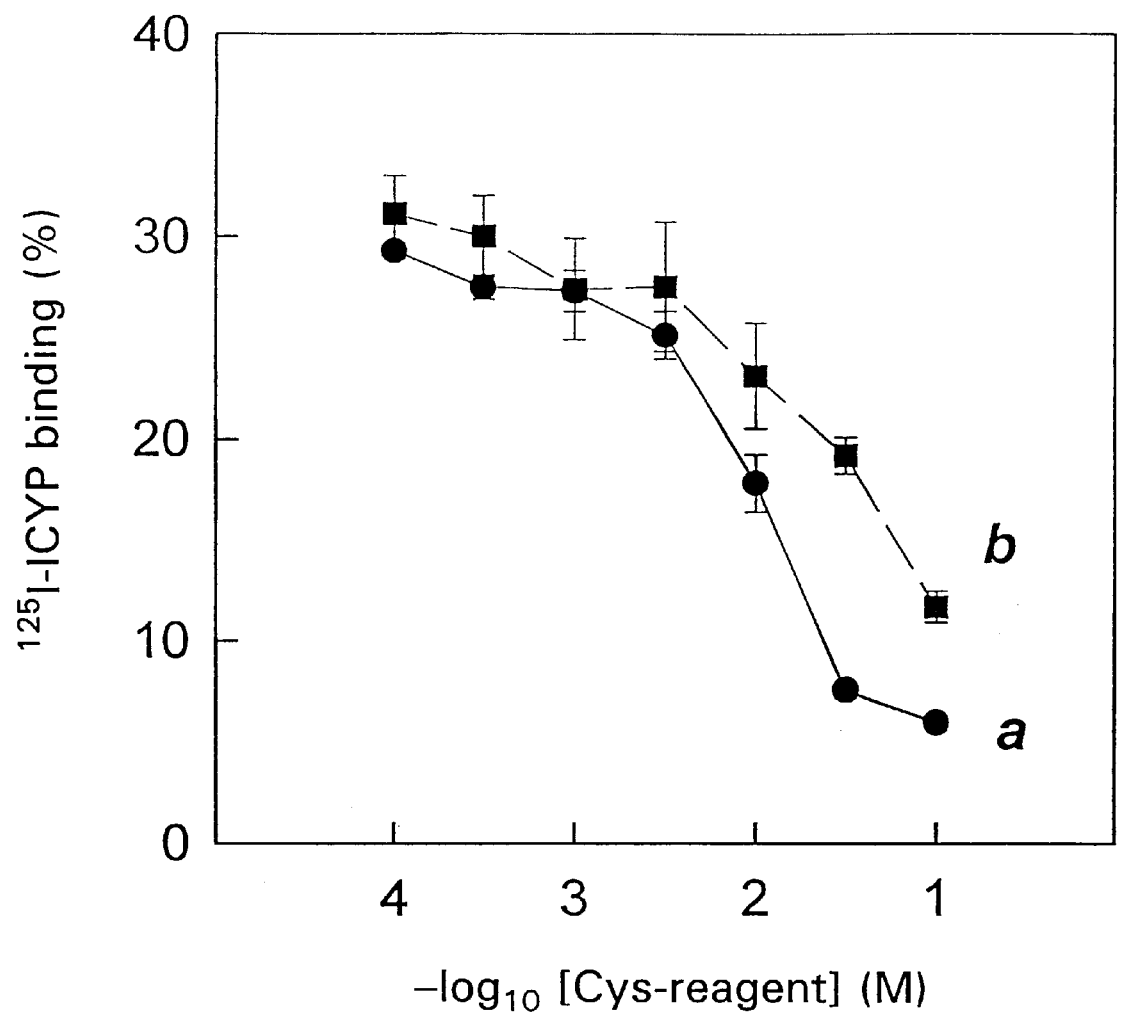
FIG. 8 shows the effects of NEM and DTT on the radioligand receptor assay using the $\beta_2$-adrenergic receptor.

$^{125}$I-ICYP binding curves with the receptor in the presence of different quantities of NEM (a) or DTT (b) are represented in FIG. 8.

Figure 9:
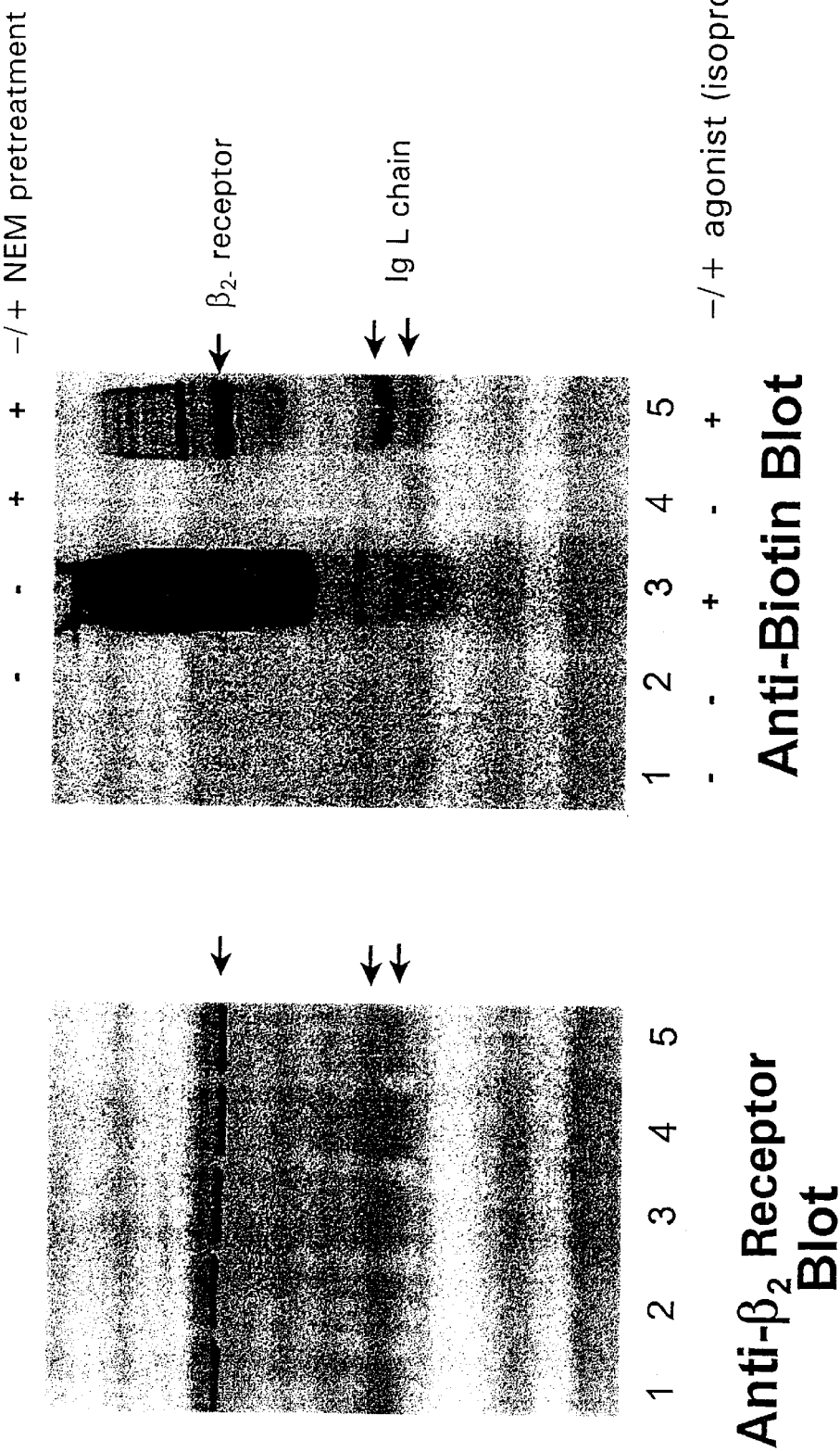
FIG. 9 shows the results of Western Blots with respect to the detection of the $\beta_2$-adrenergic receptor and the binding of biotin to the receptor.

FIG. 9 shows the results of the Western Blots with respect to the detection of the β$_2$-adrenergic receptor as a control (anti-β$_2$-adrenergic receptor blot) as well as the detection of the cysteine-specific labeling agent NEM-biotin bound to the β$_2$-adrenergic receptor. A431 cells were incubated for 10 minutes with (columns 4 and 5) and without (columns 1, 2 and 3) NEM (10 mM). After removing the NEM solutions and washing the cells, the cells were incubated with 100 μM (−)-isoproterenol for 5 min (columns 3 and 5). This was followed by one hour of incubation with 1 mM NEM-biotin (columns 2 to 5), wherein (−)-isoproterenol was still present for columns 3 and 5. After treatment with RIPA buffer, the β$_2$-adrenergic receptor was immunoprecipitated by means of anti-β$_2$-adrenergic receptor antibodies. The immunoprecipitate was divided into two fractions which were both further treated by SDS PAGE. The separated proteins were transferred to PVDF membranes for the Western blots (anti-β$_2$-adrenergic receptor blot and anti-biotin blot). Detection was effected by using a second enzyme-coupled antibody (anti-Ig). The β$_2$-adrenergic receptor shows a characteristic pattern of bands (anti-β$_2$-adrenergic receptor blot) consisting of a specific band, which pattern remained unaffected by the NEM treatment. The labeling of the receptor with NEM-biotin can only be detected if the agonist has been added. SH groups made accessible by a ligand-induced activation and/or conformational change of the receptor are now evidently labeled by NEM-biotin. A comparison between the columns 3 and 5 shows that the NEM pretreatment advantageously increases the specificity of the detection reaction.

Figure 10:
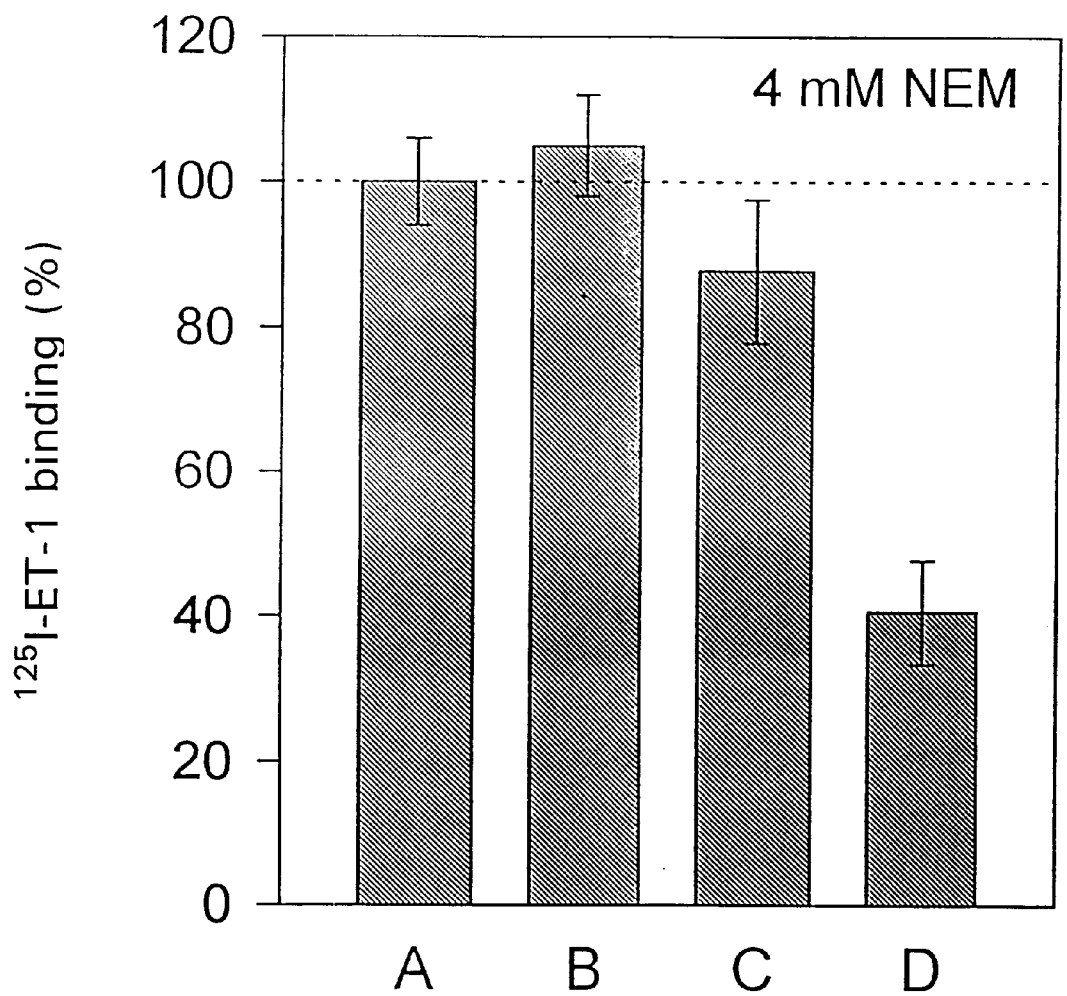
FIG. 10 shows the effect of NEM on the interaction of $^{125}$I-labeled endothelin-1 with the endothelin (ETA) receptor.

FIG. 10 illustrates the effect of NEM on the interaction of a ligand with the endothelin receptor. $^{125}$I labeled endothelin-1 (B) and human endothelin receptor (C) were incubated at room temperature with 4 mM NEM for 20 min. After dilution or washing steps, untreated receptor or radioligand was added. The assay was incubated at 30° C. over night, and the receptor fraction was subsequently precipitated for determining the bound $^{125}$I-endothelin. The pretreatment of the agonist or the receptor with NEM has only a small effect on the binding. (D) shows the result of an assay performed in the presence of 4 mM NEM, neither the hormone nor the receptor fraction having previously been pretreated with NEM. (A) shows the control incubation without any NEM incubation.

Figure 11:
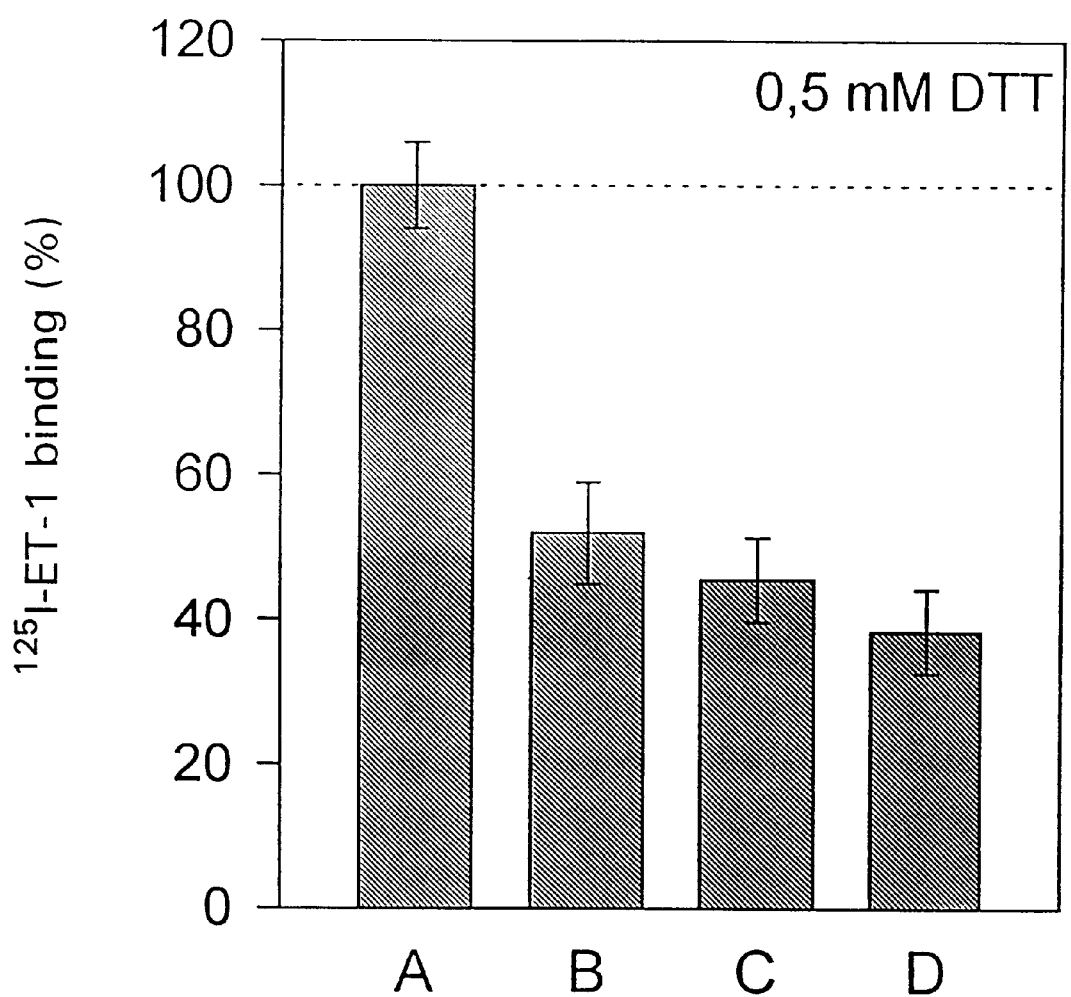
FIG. 11 shows the effect of DTT on the interaction of $^{125}$I-labeled endothelin-1 with the endothelin (ETA) receptor.

FIG. 11 illustrates the effect of DTT on the interaction of a ligand with the endothelin receptor. $^{125}$I labeled endothelin-1 (B) and human endothelin receptor (C) were incubated at room temperature with 0.5 mM DTT for 20 min. After dilution or washing steps, untreated receptor or radioligand was added. The assay was incubated at 30° C. over night, and the receptor fraction was subsequently precipitated for determining the bound $^{125}$I-endothelin. The pretreatment of the agonist or the receptor with DTT has an effect on the binding. (D) shows the result of an assay performed in the presence of 0.5 mM DTT, neither the hormone nor the receptor fraction having previously been pretreated with DTT. (A) shows the control incubation without any DTT incubation.

Figure 12:
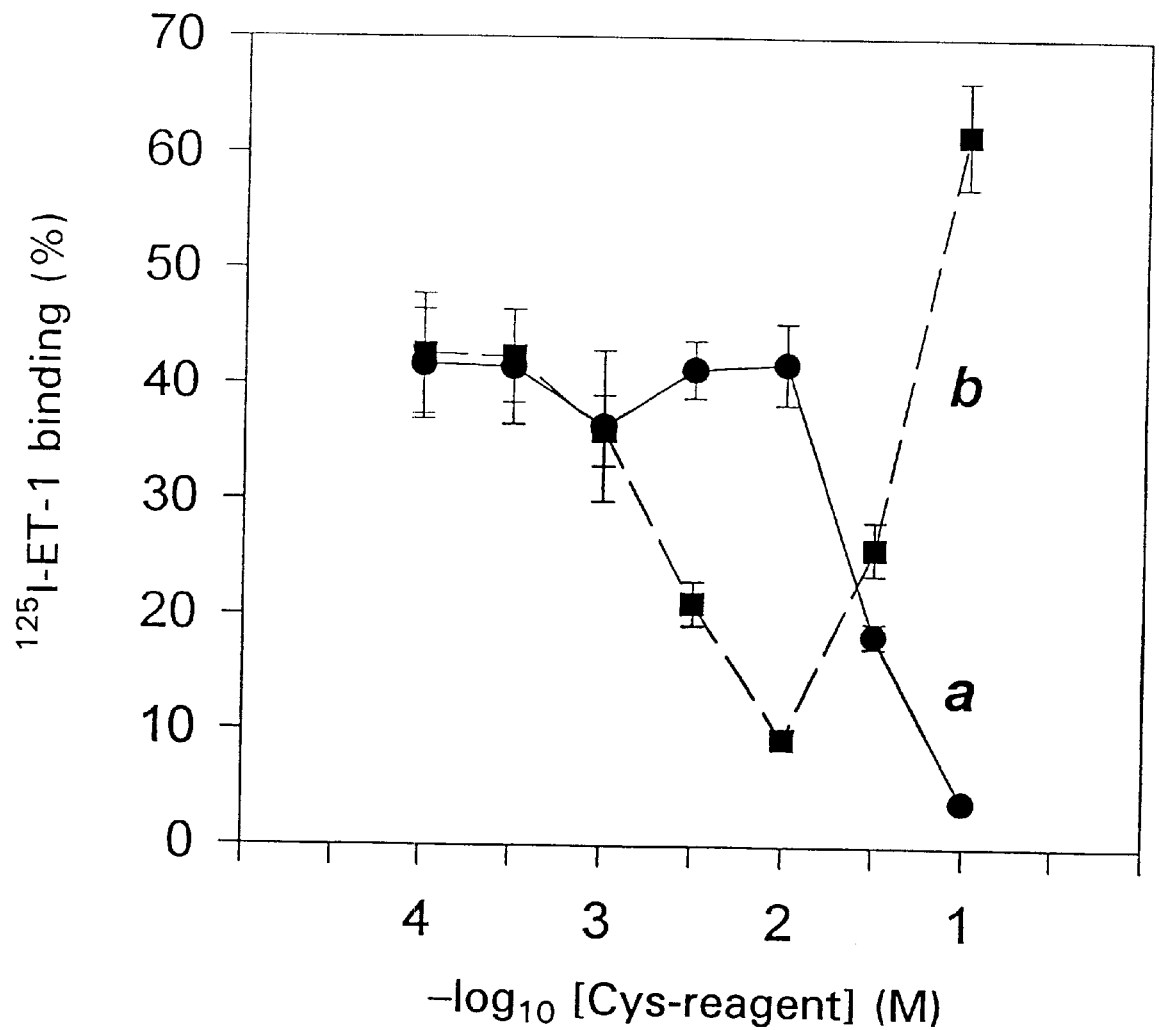
FIG. 12 shows the effects of NEM and DTT on the radioligand ETA receptor assay using the ETA receptor.

$^{125}$I-endothelin binding curves with the receptor in the presence of different quantities of NEM (a) or DTT (b) are represented in FIG. 12. The disulfide bridges of $^{125}$I-endothelin are evidently disrupted at high DTT concentrations.

Figure 13:
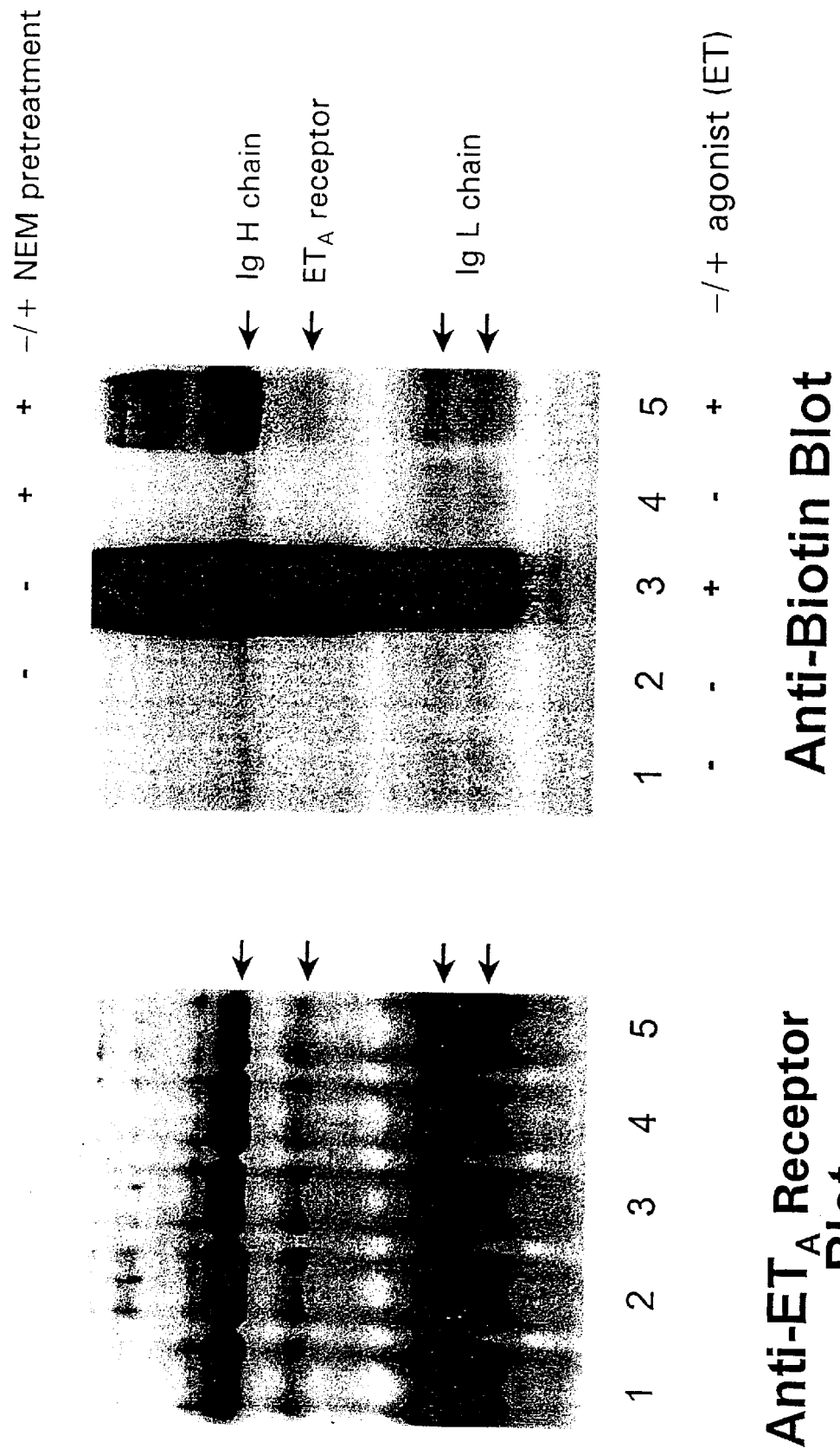
FIG. 13 shows the results of Western Blots with respect to the detection of the ETA receptor and the binding of biotin to the receptor.

FIG. 13 shows the results of the Western Blots with respect to the detection of the endothelin receptor as a control (anti-endothelin receptor blot) as well as the detection of the cysteine-specific labeling agent NEM-biotin bound to the endothelin receptor. RAT2 cells were incubated for 10 minutes with (columns 4 and 5) and without (columns 1, 2 and 3) NEM (10 mM).

After removing the NEM solutions and washing the cells, the cells were incubated with 3 nM endothelin for 10 min (columns 3 and 5). This was followed by two hours of incubation with 1 mM NEM-biotin (columns 2 to 5), wherein endothelin was still present for columns 3 and 5. After treatment with RIPA buffer, the endothelin receptor was immunoprecipitated by means of anti-endothelin receptor antibodies. The immunoprecipitate was divided into two fractions which were both further treated by SDS PAGE. The separated proteins were transferred to PVDF membranes for the Western blots (anti-endothelin receptor and anti-biotin). Detection was effected by using a second enzyme-coupled antibody (anti-Ig). The endothelin receptor shows a characteristic pattern of bands (anti-endothelin receptor blot) consisting of a specific band, which pattern remained unaffected by the NEM treatment. The labeling of the endothelin receptor with NEM-biotin can only be detected if the agonist has been added. SH groups made accessible by a ligand-induced activation and/or conformational change of the receptor are now evidently labeled by NEM-biotin. In this case too, it is found that the NEM pretreatment advantageously increases the specificity of the detection reaction (columns 3 and 5).

Figure 14:
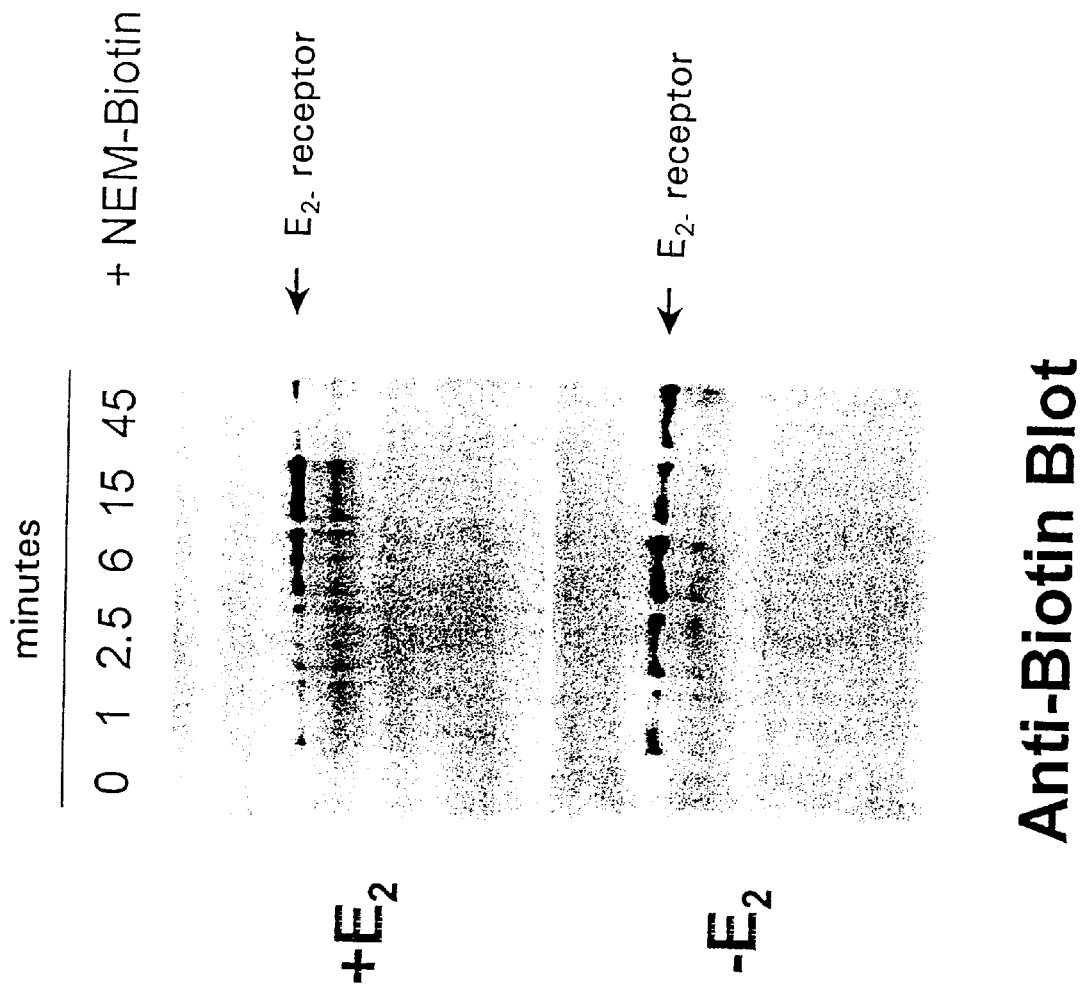
FIG. 14 shows the effect of estradiol on the binding of NEM-biotin to the human estrogen receptor α (hERα).

FIG. 14 shows the effect of estradiol on the binding of NEM-biotin to the human estrogen receptor. Further explanations are given in Example 4.

Figure 15:
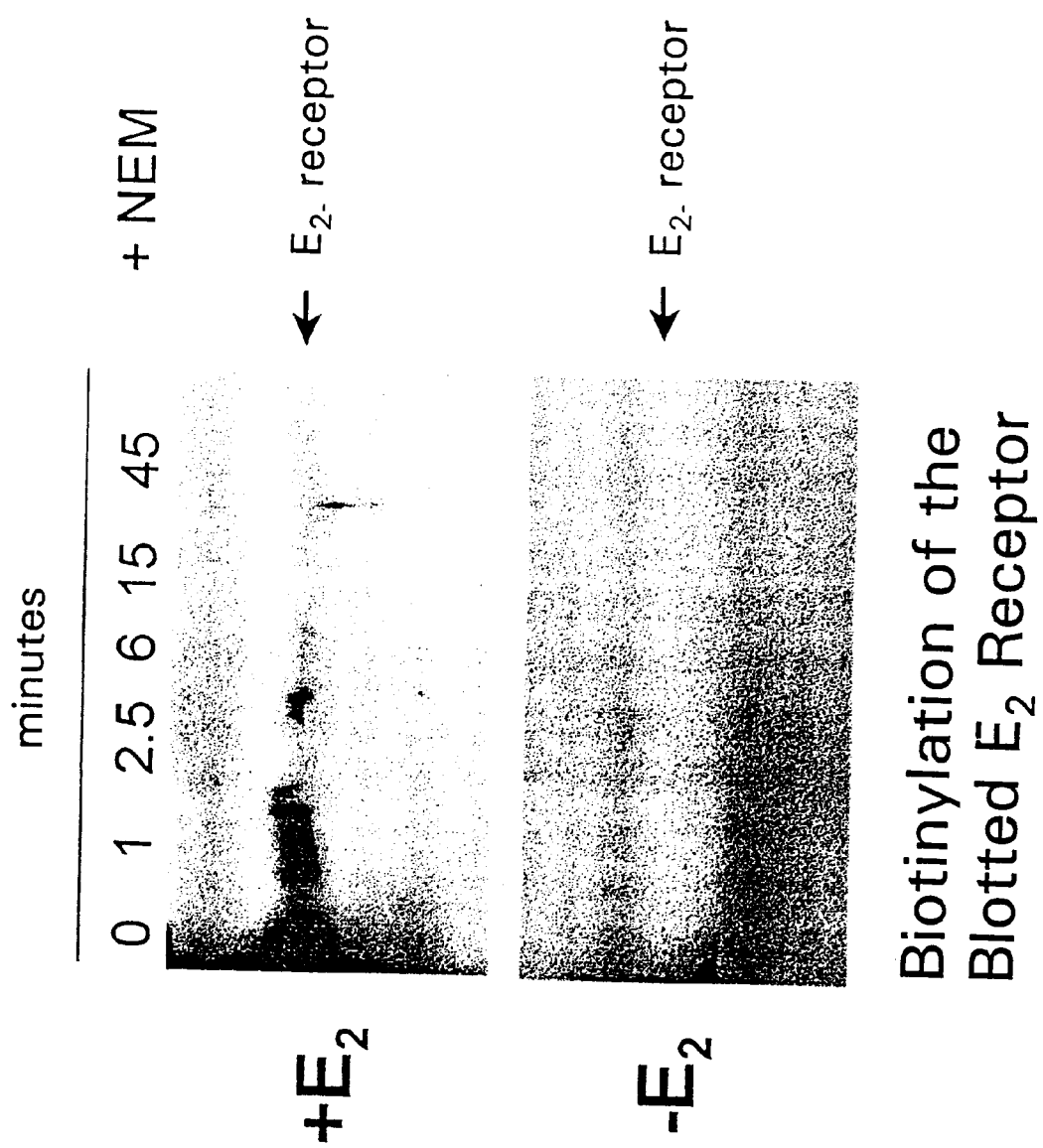
FIG. 15 shows the application of the method according to the invention to the examination of the human estrogen receptor α (hERα).

FIG. 15 shows the effect of estradiol on the accessibility of cyst(e)ines in the estrogen receptor hERα. The method according to the invention was performed here in the following order: addition of ligand (estradiol), addition of modifying agent (NEM), addition of labeling agent (NEM-biotin). Further explanations are given in Example 4.

EXAMPLE 1

Specific labeling and/or determination of conformational changes of the TSH receptor using biotinylated NEM as a cysteine-reactive labeling agent (cf. FIGS. 1 to 5).

Cells containing the TSH receptor provided with a FLAG epitope were incubated at room temperature in assay buffer (10 mM potassium phosphate with 0.1 g/l BSA, 0.01 g/l sodium azide, and 0.01 g/l phenol red, pH 7.4) with 3 mM NEM for 30 min. The excess reagent was then removed by centrifugation (1000× g, 5 min). This was followed by incubation over night with 100 μM TSH in the presence of 300 μM biotinylated NEM. The reaction efficiency of biotinylated NEM was previously established in a separate assay and corresponded to that of NEM. Then, the receptor fraction was centrifuged twice (2×10000× g, 2 min), the supernatants were removed, and the cells were covered with 1 ml of cold protein lysis buffer (25 mM Tris-HCl, pH 7.6, 150 mM NaCl, 0.1 g/l Nonident P-40 with 1 tablet of Boehringer "Complete Protease Inhibitor Complex"). After 20 minutes of incubation at 4° C. on ice, the cells were scraped off, and undesired components were pelletized by centrifugation (10000× g, 2 min). To 250 μl of the cell lysate was added 5 μl of the anti-FLAG antibody, followed by incubation at 4° C. for 60 min. After centrifugation (10000× g, 15 min, 4° C.) and removing the supernatant, protein A sepharose beads were added. This was followed by another 60 minutes of incubation at 4° C., followed by centrifugation (6000× g, 30 s). Then, several washing steps (20 mM Tris-HCl, pH 8, 100 mM NaCl, 0.05 g/l Nonident P-40) were performed with repeated centrifugations. The pellet was resuspended in 150 μl of washing buffer. Then, to 40 μl of this sample was added 8 μl of sample buffer (50 mM Tris-HCl, pH 6.8, 4% SDS, 12% glycine, 2% β-mercaptoethanol, 0.01% SERVA Blue G). The samples were then boiled for 3 to 5 min, briefly centrifuged and subsequently separated by discontinuous 10% SDS PAGE. After the electrophoresis, the gel was removed, washed in blotting buffer (48 mM Tris, 39 mM glycine, 20% methanol, 0.037% SDS) and blotted onto a PVDF membrane. The membrane was dried over night at room temperature, and then 20% methanol was added. For reducing the background, the membrane was blocked for 1 hour (1% w/v casein hydrolysate). The blocking buffer was subsequently removed. The membrane was incubated with 10 ml of a suitable first antibody dilution (anti-biotin 1:500, and for control:anti-FLAG 1:1000, each in 20 mM Tris-HCl, pH 7.6, 137 mM NaCl, 0.05% Tween 20, 0.1% casein hydrolysate) for 1 hour, washed three times for 10 min each (20 mM Tris-HCl, pH 7.6, 137 mM NaCl, 0.05% Tween 20) and then incubated with the respective second antibody (1:4000 as peroxidase conjugates, in 20 mM Tris-HCl, pH 7.6, 137 mM NaCl, 0.05% Tween 20, 0.1% casein hydrolysate) for 1 hour. After several washings (20 mM Tris-HCl, pH 7.6, 137 mM NaCl, 0.05% Tween 20), the last washing being performed with water, 5 ml each of solutions 1 and 2 was added, and the blot was soaked therein for 60 seconds. Then, a film was placed thereon. The exposition time was determined by the signal intensity.

EXAMPLE 2

Specific labeling and/or determination of conformational changes of the $\beta_2$-adrenergic receptor using biotinylated NEM as a cysteine-reactive labeling agent (cf. FIGS. 6 to 9).

A431 fibroblasts expressing the $\beta_2$-adrenergic receptor were incubated at room temperature in DMEM (Dulbecco's modified Eagle's medium) with 1% BSA and 10 mM NEM for 10 min. The excess reagent was then removed by washing with DMEM with 1% BSA. This was followed by incubation for one hour with 100 μM (−)-isoproteronol in the presence of 1 mM biotinylated NEM. The reaction efficiency of biotinylated NEM was previously established in a separate assay. Then, the cells were removed from the culture flask by slightly scraping, and then the receptor fraction was centrifuged twice (2×10000× g, 2 min), the supernatants were removed, and the cells were covered with 1 ml of cold RIPA buffer (0.1% SDS, 1% Triton X100, 1% sodium deoxycholate, 0.15 M NaCl, 0.01 M Tris-HCl, pH 7.4, 1 mM EDTA, 1 tablet of Boehringer "Complete Protease Inhibitor Complex"). After 20 minutes of incubation at 4° C. on ice, the cells were scraped off, and undesired components were pelletized by centrifugation (10000× g, 2 min). To 1000 μl of the cell lysate was added 10 μl of Normal Rabbit Serum, followed by incubation at 4° C. for 60 min. After centrifugation (10 000× g, 15 min, 4° C.) and removing the supernatant, protein A sepharose beads were added. This was followed by another 60 minutes of incubation at 4° C. After centrifugation (10 000× g, 15 min, 4° C.) and removing the supernatant, 4 μg of the specific anti-$\beta_2$-adrenergic receptor antibody was added. This was followed by another 60 minutes of incubation at 4° C. After centrifugation (10000× g, 15 min, 4° C.) and removing the supernatant, protein A sepharose was added. This was followed by centrifugation (6000× g, 30 s). Then, several washing steps (0.1% SDS, 1% Triton X100, 1% sodium deoxycholate, 0.15 M NaCl, 0.01 M Tris-HCl, pH 7.4, 1 mM EDTA, 1 tablet of Boehringer "Complete Protease Inhibitor Complex" ) were performed with repeated centrifugations. The pellet was resuspended in 30 μl of sample buffer (50 mM Tris-HCl, pH 6.8, 4% SDS, 12% glycine, 2% β-mercaptoethanol, 0.01% SERVA Blue G). The samples were then boiled for 3 to 5 min, briefly centrifuged and subsequently separated by discontinuous 10% SDS PAGE. After the electrophoresis, the gel was removed, washed in blotting buffer (48 mM Tris, 39 mM glycine, 20% methanol, 0.037% SDS) and blotted onto a PVDF membrane. The membrane was dried over night at room temperature, and then 20% methanol was added. For reducing the background, the membrane was blocked for 1 hour (1% w/v casein hydrolysate). The blocking buffer was subsequently removed. The membrane was incubated with 10 ml of a suitable first antibody dilution (anti-biotin 1:2500, and for control: anti-$\beta_2$-adrenergic receptor 1:1000, each in 20 mM Tris-HCl, pH 7.6, 137 mM NaCl, 0.05% Tween 20, 0.1% casein hydrolysate) for 1 hour, washed three times for 10 min each (20 mM Tris-HCl, pH 7.6, 137 mM NaCl, 0.05% Tween 20) and then incubated with the respective second antibody (1:2500 as peroxidase conjugates, in 20 mM Tris-HCl, pH 7.6, 137 mM NaCl, 0.05% Tween 20, 0.1% casein hydrolysate) for 1 hour. After several washings (20 mM Tris-HCl, pH 7.6, 137 mM NaCl, 0.05% Tween 20), the last washing being performed with water, 5 ml each of ECL solutions 1 and 2 was added, and the blot was soaked therein for 60 seconds. Then, a film was placed thereon. The exposition time was determined by the signal intensity.

EXAMPLE 3

Specific labeling and/or determination of conformational changes of the endothelin receptor using biotinylated NEM as a cysteine-reactive labeling agent (cf. FIGS. 10 to 13).

RAT2 fibroblasts expressing the endothelin receptor were incubated at room temperature in DMEM (Dulbecco's modified Eagle's medium) with 1% BSA and 10 mM NEM for 10 min. The excess reagent was then removed by washing with DMEM with 1% BSA. This was followed by incubation for 2 hours with 3 nM endothelin in the presence of 1 mM biotinylated NEM. The reaction efficiency of biotinylated NEM was previously established in a separate assay. Then, the cells were removed from the culture flask by slightly scraping, and then the receptor fraction was centrifuged twice (2×10000× g, 2 min), the supernatants were removed, and the cells were covered with 1 ml of cold RIPA buffer (0.1% SDS, 1% Triton X100, 1% sodium deoxycholate, 0.15 M NaCl, 0.01 M Tris-HCl, pH 7.4, 1 mM EDTA, 1 tablet of Boehringer "Complete Protease Inhibitor Complex"). After 20 minutes of incubation at 4° C. on ice, the cells were scraped off, and undesired components were pelletized by centrifugation (10000× g, 2 min). To 1000 μl of the cell lysate was added 10 μl of either Normal Rabbit Serum or Normal Sheep Serum (depending on the primary anti-receptor antibody employed), followed by incubation at 4° C. for 60 min. After centrifugation (10 000× g, 15 min, 4° C.) and removing the supernatant, protein G sepharose beads were added. This was followed by another 60 minutes of incubation at 4° C. After centrifugation (10 000× g, 15 min, 4° C.) and removing the supernatant, 4 μg of the specific anti-endothelin receptor antibody was added. This was followed by another 60 minutes of incubation at 4° C. After centrifugation (10 000× g, 15 min, 4° C.) and removing the supernatant, protein G sepharose was added. This was followed by centrifugation (6000× g, 30 s). Then, several washing steps (0.1% SDS, 1% Triton X100, 1% sodium deoxycholate, 0.15 M NaCl, 0.01 M Tris-HCl, pH 7.4, 1 mM EDTA, 1 tablet of Boehringer "Complete Protease Inhibitor Complex") were performed with repeated centrifugations. The pellet was resuspended in 30 μl of sample buffer (50 mM Tris-HCl, pH 6.8, 4% SDS, 12% glycine, 2% β-mercaptoethanol, 0.01% SERVA Blue G). The samples were then boiled for 3 to 5 min, briefly centrifuged and subsequently separated by discontinuous 10% SDS PAGE. After the electrophoresis, the gel was removed, washed in blotting buffer (48 mM Tris, 39 mM glycine, 20% methanol, 0.037% SDS) and blotted onto a PVDF membrane. The membrane was dried over night at room temperature, and then 20% methanol was added. For reducing the background, the membrane was blocked for 1 hour (1% w/v casein hydrolysate). The blocking buffer was subsequently removed. The membrane was incubated with 10 ml of a suitable first antibody dilution (anti-biotin 1:2500, and for control: anti-endothelin receptor 1:1000, each in 20 mM Tris-HCl, pH 7.6, 137 mM NaCl, 0.05% Tween 20, 0.1% casein hydrolysate) for 1 hour, washed three times for 10 min each (20 mM Tris-HCl, pH 7.6, 137 mM NaCl, 0.05% Tween 20) and then incubated with the respective second antibody (1:2500 as peroxidase conjugates, in 20 mM Tris-HCl, pH 7.6, 137 mM NaCl, 0.05% Tween 20, 0.1% casein hydrolysate) for 1 hour. After several washings (20 mM Tris-HCl, pH 7.6, 137 mM NaCl, 0.05% Tween 20), the last washing being performed with water, 5 ml each of ECL solutions 1 and 2 was added, and the blot was soaked therein for 60 seconds. Then, a film was placed thereon. The exposition time was determined by the signal intensity.

EXAMPLE 4

Specific labeling and/or determination of conformational changes of the human estrogen receptor (hERα) using biotinylated NEM as a cysteine-reactive labeling agent.

The human estrogen receptor α (hERα) was expressed as a recombinant protein in baculovirus infected Sf9 cells and purified by 17β-estradiol agarose chromatography. 2 μg of the affinity-purified hERα in 50 mM Tris, pH 7.5, 10% glycerol, 0.5 M KCl, 1 mM EDTA, 2 mM DTT, 1 mM sodium vanadate and 0.02% sodium azide was diluted to a concentration of 2 ng/μl in 1 ml of TEG buffer (10 mM Tris, 10% glycerol, 1 mM EDTA, 0.5 mM DTT) at pH 8.0 and divided into two equal fractions. To one of the fractions was added 50 ml of TEG buffer ("minus estradiol", $-E_2$), and to the other fraction was added 50 μl of 17β-estradiol in TEG buffer ("plus estradiol", $+E_2$) to reach an estradiol concentration of 200 μM. Saturation of the ligand binding domain was achieved by 20 minutes of incubation at room temperature. Then, the incubation was cooled down. All subsequent steps were performed at 4° C. in order to reduce the dissociation rate of the hormone receptor complex to a low level. The "minus" and "plus" estradiol aliquots were further divided into 2 fractions each. To one of the "minus"/"plus" pairs was added 10 μl of a 55 mM NEM solution (in ethanol) to reach an effective concentration of 2.2 mM. To the other "minus"/"plus" pair was added 10 μl of a 55 mM NEM-biotin solution (in DMSO) to reach an effective concentration of 2.2 mM; the time dependence of the alkylation reaction was to be followed. This moment is considered time "0". 50 μl of the different incubations were removed at particular times (up to 45 min), and 10 μl of sample buffer (50 mM Tris-HCl, pH 6.8, 4% SDS, 12% glycine, 2% β-mercaptoethanol, 0.01% SERVA Blue G) was added. The molar excess of β-mercaptoethanol prevented further alkylation of the receptor and inactivated residual NEM and NEM-biotin in the reaction mixture. The reaction rate for the modification of the available cysteine sulfhydryl groups was followed by their biotinylation and detected by means of subsequent Western blots (FIG. 14). The "minus"/"plus" pair to which NEM had been added was also subjected to PAGE and blotted onto PVDF membrane. The membrane was dried over night at room temperature, and then 20% methanol was added. hERα was biotinylated directly on the PVDF membrane (1.7 mM NEM-biotin in TEG buffer, 20 min); see FIG. 15. The reaction was quenched by repeatedly washing the membrane with TBS-T (20 mM Tris-HCl, pH 7.6, 137 mM NaCl, 0.05% Tween 20). For reducing the background, the membrane was blocked for 1 hour (1% w/v casein hydrolysate). The blocking buffer was subsequently removed. The membrane was incubated with 10 ml of a suitable antibody dilution (anti-biotin 1:2500 as a peroxidase conjugate in 20 mM Tris-HCl, pH 7.6, 137 mM NaCl, 0.05% Tween 20, 0.1% casein hydrolysate) for 1 hour, washed three times for 10 min each (20 mM Tris-HCl, pH 7.6, 137 mM NaCl, 0.05% Tween 20) and finally washed with water. Then, 5 ml each of ECL solutions 1 and 2 was added, and the blot was soaked therein for 60 seconds. Then, a film was placed thereon. The exposition time was determined by the signal intensity.

What is claimed is:

1. A method for the specific labeling of a protein containing selenocyst(e)ine and/or cyst(e)ine groups, comprising the following steps:

at least one incubation of a protein-containing sample with at least one modifying agent specific for selenocyst(e)ine and/or cyst(e)ine groups, followed by at least one further incubation of said protein-containing sample with at least one labeling agent specific for selenocyst(e)ine and/or cyst(e)ine groups;

wherein at least one substance interacting with said protein is added prior to and/or during and/or after at least one of said incubations.

2. The method according to claim 1, characterized in that said modifying agent specific for selenocyst(e)ine and/or cyst(e)ine groups will alkylate these groups.

3. The method according to any of claim 1, characterized in that said labeling agent specific for selenocyst(e)ine and/or cyst(e)ine groups will alkylate these groups.

4. The method according to claim 1, characterized in that said modifying agent is N-ethylmaleinimide, dithiothreitol, dithioerythritol, β-mercaptoethanol, iodoacetamide, iodoacetate, diamide or p-CMB.

5. The method according to claim 1, characterized in that said labeling agent is a derivative of said modifying agent.

6. The method according to claim 1, characterized in that said labeling agent is luminescent and/or contains at least one luminophor and/or contains a affinity ligand.

7. The method according to claim 1, characterized in that said protein has enzymatic activity and/or is a receptor, a transmembrane receptor, a 7-transmembrane receptor, or a soluble protein receptor.

8. The method according to claim 1, characterized in that said modifying agent and/or said labeling agent is added in excess.

9. The method according to claim 1, characterized in that excess modifying agent is removed or inactivated prior to said incubation with the labeling agent.

10. The method according to claim 1, characterized in that said specific labeling of the protein is detected by a Western blot method.

11. The method according to claim 1, characterized in that said specific labeling of the protein is detected by spectroscopical methods, using a detection system based on confocal fluorescence spectroscopy, fluorescence correlation spectroscopy, and/or near-field spectroscopy.

12. A screening method for determining substances which interact with a protein, wherein said protein and said substance are employed in the method according to claim 1 and the labeling of the protein is detected.

13. A screening method for determining proteins which interact with a substance, wherein said proteins and said substance are employed in the method according to claim 1 and the labeling of the protein is detected.

14. A method for the detection of the activation or deactivation and/or for determining conformational changes of proteins using substances which interact with said proteins, wherein said proteins and said substances are employed in the method according to claim 1 and the labeling of the protein is detected.

* * * * *